United States Patent [19]

Olah

[11] 4,288,646

[45] Sep. 8, 1981

[54] REGIOSELECTIVE PREPARATION OF β-ISOPROPYLNAPHTHALENE OVER SUPERACIDIC SOLID OR SUPPORTED PERFLUORINATED SULFONIC ACID CATALYSTS

[75] Inventor: George A. Olah, Beverly Hills, Calif.

[73] Assignee: PCUK Produits Chimiques Ugine Kuhlmann, Courbevoie, France

[21] Appl. No.: 82,164

[22] Filed: Oct. 5, 1979

[51] Int. Cl.³ ............................................. C07C 2/66
[52] U.S. Cl. ................................... 585/458; 585/471
[58] Field of Search ............................... 585/458, 471

[56] References Cited

U.S. PATENT DOCUMENTS

| 2,776,322 | 1/1957 | Webster et al. | 260/621 |
|---|---|---|---|
| 2,837,583 | 6/1958 | Lien et al. | 585/472 |
| 3,251,897 | 5/1966 | Wise | 585/455 |
| 3,458,587 | 7/1969 | Suld | 585/320 |
| 3,504,045 | 3/1970 | Scharf et al. | 585/477 |
| 3,504,046 | 3/1970 | Scharf et al. | 585/466 |
| 3,845,149 | 10/1974 | Pietzsch et al. | 585/477 |
| 3,886,233 | 5/1975 | Visseren | 260/878 R |
| 4,022,847 | 5/1977 | McClure | 585/458 |
| 4,026,959 | 5/1977 | Kemme et al. | 585/320 |

FOREIGN PATENT DOCUMENTS 936089 12/1955 Fed. Rep. of Germany .
1274097 8/1968 Fed. Rep. of Germany .
263583 2/1970 U.S.S.R. .

OTHER PUBLICATIONS

Olah et al., J.A.C.S., 98, 1839 (1976).
Friedman et al., J. Org. Chem., 34, 3211 (1969).
Haworth et al., J.A.C.S., 1790 (1932).
Price et al., J.A.C.S., 60, 2499, (1938).
Foberov et al., Doklady Akad. Nauk SSSR 179, 1359 (1968).
Bichurine et al., Tr. Nauk Inst. Nefterkhim, 1970, No. 2, 71.
Topchiev et al., Doklady Akad. Nauk SSSR, 139 124 (1961).

Primary Examiner—Curtis R. Davis
Attorney, Agent, or Firm—Pennie & Edmonds

[57] ABSTRACT

A process for the production of β-isopropylnaphthalene in high regioselectivity (90-98%) by alkylation of naphthalene over solid or supported superacid catalysts, such as a perfluorinated alkanesulfonic acid of four to eighteen carbon atoms ($C_4F_9SO_3H$ to $C_{18}F_{37}SO_3H$) or a polymeric perfluorinated resin-sulfonic acid, such as the acid form of the commercially available Nafion-K ion-membrane resin (DuPont). Further isomerization of mixtures of isomeric isopropylnaphthalenes to preferentially pure β-isopropylnaphthalene can also be effected.

8 Claims, No Drawings

REGIOSELECTIVE PREPARATION OF β-ISOPROPYLNAPHTHALENE OVER SUPERACIDIC SOLID OR SUPPORTED PERFLUORINATED SULFONIC ACID CATALYSTS

TECHNICAL FIELD

Isopropylation of naphthalene over solid supported perfluorinated sulfonic acid catalysts giving regioselectively β-isopropylnaphthalene.

BACKGROUND ART

The manufacture of β-naphthol, according to the Hock process, necessitates β-isopropylnaphthalene, which is subsequently oxidized to α-hydroxyperoxypropyl-2-naphthalene and treated with acid to undergo rearrangement-cleavage to give β-naphthol and acetone.

Preparation of β-isopropylnaphthalenes in solution is generally carried out by Friedel-Crafts type of alkylation processes using either Lewis acid halide catalysts, such as aluminum chloride, or over solid catalysts, such as supported phosphoric acid or aluminosilicates. All these reactions generally yield a mixture of α- and β-isopropylnaphthalene, which subsequently needs to be separated and/or further isomerized. Further, aluminum chloride and the like Friedel-Crafts catalysts form highly colored complexes with the products, which must be decomposed upon work-up, resulting generally in loss of the catalyst and significant cost.

It was shown in studies of solution Friedel-Crafts isopropylation of naphthalene that mixtures of α- and β-products are obtained (see "Friedel-Crafts and Related Reactions", ed. G. A. Olah, Vol. 11, Chapter XIV, Wiley-Interscience Publishers, New York, New York, 1964; H. E. Nürsten and A. T. Peters, Journal of the Chemical Society (London) 129 (1950), G. A. Olah and J. A. Olah, Journal of the American Chemical Society 1976, 98, 1839.

Haworth, Letsky and Marvin, (Journal of Chemical Society, 1932, p. 1790) claimed to have obtained pure β-isopropylnaphthalene by the reaction of isopropyl bromide with naphthalene in the presence of aluminum chloride, as did Price and Ciskowsky (Journal of the American Chemical Society, 60, 2499) in the reaction of 2-propanol and naphthalene using boron trifluoride as catalyst. U.S. Pat. No. 2,776,322 (W. Webster and D. Cheselden, 1957), however, demonstrated that these reactions, as well as related aluminum chloride catalyzed isopropylation with propene gave mixtures of α- and β-isomers, which must be separated either by careful, very efficient fractional distillation or by crystallization.

Subsequently, the Friedel-Crafts alkylation of naphthalene with propene using $H_3PO_4 \cdot BF_3$ catalyst was reported to give 70% α- and 30% β-isopropylnaphthalene (Friedman and Nelson, Journal of Organic Chemistry, 34, 3211 (1969). It was more recently shown in mechanistic studies with aluminum trichloride using dilute $CS_2$ or $CH_3NO_2$ solution with short reaction times and very low conversions that kinetic conditions tend to favor formation of the α-isomer, whereas thermodynamic conditions favor the β-isomer. The thermodynamic equilibrium of the $AlCl_3$ catalyzed solution isomerization of isopropylnaphthalenes was also established (Olah and Olah, Journal of the American Chemical Society, Vol. 98, 1839 (1976). However, so far no practical regioselective preparation of β-isopropylnaphthalene has been achieved. U.S. Pat. No. 2,776,322, for example, clearly states that isopropylnaphthalenes obtained by Friedel-Crafts reactions are mixtures of the α- and β-isomers, which need to be separated by highly efficient distillation or crystallization. U.S. Pat. No. 3,458,587 describes the catalytic liquid phase alkylation of naphthalene with propene over solid $H_3PO_4$ to give mixtures of α- and β-isopropylnaphthalenes which subsequently in a separate operation are isomerized by anhydrous hydrogen fluoride to give a higher ratio of the needed β-isomer. U.S. Pat. No. 3,504,045 also teaches that Friedel-Crafts alkylation of naphthalene gives a mixture of the α- and β-isomers. The content of the β-isomer is increased by treatment of the alkylate with $H_3PO_4$ over a solid support at elevated temperature. The product distribution at 350° C. was 13% α- and 52.5% β-iospropylnaphthalene, together with 16% naphthalene and 18% higher molecular weight polymeric products. U.S. Pat. No. 3,504,046 teaches alkylation of naphthalene over similar $H_3PO_4$ catalyst on solid support. At 350° C. at 800 psig propene, a product mixture consisting 16% naphthalene, 17% α- and 34.8% β-isopropylnaphthalene was obtained.

The prior art of the alkylation of naphthalene is summarized in recent U.S. Pat. No. 4,026,959 (1977) describing an isomerization process for isopropylnaphthalenes. It states, "Thus, there is no method of which we are aware to efficiently produce isopropylnaphthalene in high yield and high beta isomer content and with economic use of catalyst by direct alkylation of naphthalene with propylene. This is true regardless of the catalyst used as far as we are aware. There remains, therefore, a need for an economic process for the preparation of beta-isopropylnaphthalene in high yield and high purity, from naphthalene and propene" (as well as other alkylating agents). The present invention discloses such a method.

DISCLOSURE OF THE INVENTION

The present invention relates to the isopropylation of naphthalene over solid or supported perfluorinated sulfonic acid catalysts giving regioselectively β-isopropylnaphthalene generally in high (90-98+%) isomeric purity suitable for the manufacture of β-naphthol without any further purification, separation, or subsequent isomerization. The invention includes a process of converting mixtures of α- and β-isopropylnaphthalenes, from any source, into essentially pure β-isopropylnaphthalenes.

The fact that Friedel-Crafts alkylations in solution, with catalysts such as aluminum chloride, are generally accompanied by formation of highly colored complexes (red oils), results in the need to use large amounts (molar excess) of the catalyst, which is to a large extent tied up as the counter-ion of the carbocationic complexes. These complexes must be decomposed upon workup, resulting in loss of the anhydrous halide catalysts. The use of solid or supported superacidic perfluorinated sulfonic acid catalysts, according to this invention, results in no complex formation and thus, there is no need for any particular workup of the reaction mixtures. Whereas previously utilized solid acid catalysts were not of sufficient strength to allow regioselective preparation of β-isopropylnaphthalene, use of superacidic solid perfluorinated sulfonic acid catalysts allows such preparation with all the mentioned advantages.

BEST MODE FOR CARRYING OUT THE INVENTION

The present invention allows the regioselective preparation of β-isopropylnapththalene in high (90-98+%) purity by reacting naphthalene with a suitable alkylating agent, such as 2-halopropanes, propene, 2-propanol, esters of 2-propanol, such as 2-propyl chloroformate, propylated aromatics, such as cumene, cymenes, di- and polyisopropylnaphthalenes, and the like. The reactions can be carried out either in solution in a high boiling solvent, such as decaline, or in the gas phase by reacting naphthalene with the corresponding alkylating agent over a solid or supported perfluorinated sulfonic acid catalyst, such as higher molecular weight perfluorinated alkanesulfonic acids, preferentially of $C_6$ to $C_{18}$ carbon atoms, or the acid form of a perfluorinated resinsulfonic acid ion-membrane resin, such as the commercially available Nafion-K (DuPont) ion-membrane resin. This perfluorinated resinsulfonic acid comprises a fluorinated polymer having sulfonic acid groups in the amount of about 0.01 to 5 mequiv/gram catalyst. The polymer catalyst contains a repeating structure, which can be depicted as:

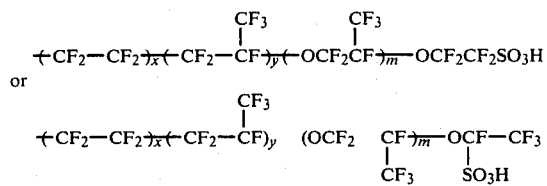

where the ratio of x over y varies from about 2 to about 50, and m is 1 or 2. This polymer structure is available commercially under the tradename Nafion resin. Polymer catalysts of the above structure can be prepared in various ways. One method, disclosed in Conolly et al. U.S. Pat. No. 3,282,875 and Cavanaugh et al. U.S. Pat. No. 3,882,093 comprises polymerizing the corresponding perfluorinated vinyl compounds. It is also possible to prepare polymer catalyst according to U.S. Pat. No. 4,041,090 by copolymerizing the corresponding perfluorinated vinyl ethers with perfluoroethylene and/or perfluoro-alpha-olefins. The specific fluorinated repeating structure depicted above is not critical but perfluorinated is preferred.

The isopropylation of naphthalene with the aforementioned solid superacid catalysts giving 90 to 98+% β- isopropylnaphthlene, is generally carried out at temperatures between 150° and 250° C., preferentially between 170° and 220° C., at atmospheric or slightly superatmospheric (up to about 10 atm) pressure. Table I illustrates the high β-regioselectivity obtained in propylation of naphthalene based on the specific examples put forward to illustrate the invention. A further aspect of the present invention is the ability of the solid superacid catalysts to effect trans-isopropylation reactions of naphthalene with propylated aromatics. Thus, naphthalene, when reacted with isopropylated aromatics, such as isopropylbenzene, isopropyltoluenes or di- and polyisopropylnaphthalene mixtures, gives β-isopropylnaphthalene in high regioselectivity yield.

It is an even further aspect of the invention that any mixture of α- and β-isopropylnaphthalenes can be also converted into essentially pure β-isopropylnaphthalene when treated with the solid superacid catalysts at temperatures ranging from 150° to 250° C., preferentially between 170° and 220° C., in the same manner with the absence of the naphthalene reactant.

The scope of the invention is further described in connection with the following examples, which are set forth for the purpose of illustration and are not to be considered to limit the scope of the invention in any manner.

EXAMPLE 1

10 g of a perfluorodecanesulfonic acid $C_{10}F_{21}SO_3H$ was deposited via vacuum distillation on 75 g of porous chromosorb. 5 g of this catalyst was charged into a liquid-phase alkylation reactor together with 0.1 mol of naphthalene dissolved in 150 ml of decaline. Through the stirred solution, close to its boiling point (190° C.) propylene was passed through at a rate of 0.8 l/min. for one hour. Thereafter, the solution was stirred at the same temperature for one additional hour. After cooling, the catalyst was filtered off and the solution distilled in vacuum. The yield of isopropylnaphthalene obtained was 68% with an isomer composition of 92% β- and 8% α-isomer (analyzed by gas-liquid chromatorgraphy).

EXAMPLE 2

Reaction was carried out as in Example 1, but using 2-bromopropane as the alkylating agent. A 38% yield of isopropylnaphthalenes was obtained, with an isomer composition of 88% β- and 12% α-isopropylnaphthalene.

EXAMPLE 3

Reaction was carried out as in Example 1, but using perfluorododecanesulfonic acid and isopropyl chloroformate as the alkylating agent. A 43% yield of isopropylnaphthalenes was obtained with an isomer composition of 92% β- and 8% α-isopropylnaphthalene.

EXAMPLE 4

Reaction was carried out as in Example 1, but using cumene to transalkylate naphthalene to isopropylnaphthalenes. A yield of 34% was obtained with an isomer composition of 89% β- and 11% α-.

EXAMPLE 5

50 g of commercial Nafion-K resin (potassium salt of the DuPont Company's ion-membrane material) was refluxed in 250 ml of deionized water for two hours. After filtering, the resin was treated with 100 ml of 20% to 25% nitric acid for 5 hours at room temperature. Filtering was followed with repeat of the nitric acid treatment three times. Finally, the resin was washed to neutrality with deionized water and dried in a vacuum drying oven at 105° C. for 24 hours. 5 g of the Nafion-H perfluorinated resinsulfonic acid catalyst was charged into the liquid-phase alkylator and the isopropylation of naphthalene was carried out in the same manner as described in Example 1. 73% isopropyl-naphthalene was obtained with composition of 95% β- and 5% α- isomer.

EXAMPLE 6

Reaction was carried out as in Example 4, but using 2-chloropropane as the alkylating agent with a molar ratio of naphthalene/2-chloropropane of 1:0.8. Yield of isopropylnaphthalene obtained was 54%, with an isomer distribution of 98% β- and 2% α-isopropylnaphthalene.

EXAMPLE 7

Reaction was carried out as in Example 4, but by reacting naphthalene with cumene in a molar ratio of 1 to 0.8 for 4 hours. Yield of isopropylnaphthalene obtained was 37%%, with an isomer distribution of 92% β- and 8% α.

EXAMPLE 8

Reaction was carried out as in Example 7, but by reacting naphthalene with p-cymene. Yield of isopropylnaphthalene obtained was 51% with 93% β- and 7% α-isomer.

EXAMPLE 9

When under the conditions of Examples 5, 20 g of an isomeric mixture of commercial isopropylnaphthalene consisting of 57% α- and 43% β-isomer was heated in 200 ml decaline solution at 190° C. over 5 g of Nafion-H catalyst for two hours, the resulting product consisted of 98% β- and 2% α-isopropylnaphthalene.

EXAMPLE 10

A fixed bed catalytic reactor of 170×12 mm dimension was charged with 2 g of active nafion-H catalyst. A continuous flow of a commercial mixture of isopropylnaphthalenes (consisting of 57% α- and 43% β-isomer) was passed, being fed by a syringe pump, at a consistent liquid rate of 0.06 ml/min. through the reaction chamber heated electrically to about 220° C., in a stream of dry nitrogen (rate 8 ml/min.). The product composition of the isomerized isopropylnaphthalenes sampled at intervals, stayed constant at 92% β- and 8% α-isomer.

EXAMPLE 11

A fixed bed catalytic reactor, similar to that of Example 10, was charged with 2.2 g of activated, as in Example 5, Nafion-H catalyst and used for the gas-phase alkylation of naphthalene with 2-chloropropane. Through the catalytic reactor kept at 220° C. by electric heating, was passed naphthalene in carbon tetrachloride or cyclohexane together with 2-chloropropane in a mole ratio of 1:0.8 fed by means of a syringe pump at a constant rate of 0.15 m./min. as a 10% solution in carbon tetrachloride and cyclohexane. Products emerging from the reactor could be directly separated by fractional distillation, precluding the need for any washing or other treatment, and were analyzed by gas-liquid chromatography. Yield of isopropylnaphthalene was 34%, with an isomer composition of 93% β- and 7% α-.

EXAMPLE 12

Reaction was carried out similarly as in Example 11, but using 2-bromopropane as the alkylating agent. A yield of 30% isopropylnaphthalenes was obtained with a composition of 92% β- and 8% α-isomer.

EXAMPLE 13

Reaction was carried out similarly as in Example 11, but using propene as the alkylating agent. Yield of isopropylnaphthalenes obtained was 37%, with 90% β- and 10% α-isomer.

EXAMPLE 14

Reaction was carried out similarly as in Example 11, but using 2-propanol as the alkylating agent. Yield of isopropylnaphthalene obtained was 39% with 92% β- and 8% α-isomer.

EXAMPLE 15

Reaction was carried out similarly as in Example 11, but using p-cymene to transalkylate naphthalene. Yield of isopropylnaphthalene obtained was 21%, with 90% β- and 10% α-isopropylnaphthalene.

While the invention has been described in connection with preferred embodiments, it is not intended to limit the invention to the particular forms set forth, but, on the contrary, it is intended to cover such alternatives, modifications, and equivalents as may be included within the spirit and scope of the invention as defined by the appended claims.

TABLE I

| | | | | | | | % Isomer | |
|---|---|---|---|---|---|---|---|---|
| | | | | | Time | % Yield | Distribution | |
| | Example | | | Temp | Over | Isopropyl- | | |
| Alkylating Agent | Number | Catalyst | Solvent | °C. | Catalyst | Naphthalene | α- | β- |
| CH$_3$CH=CH$_2$ | 1 | PDSA* | decaline | 190 | 2 hrs | 68 | 8 | 92 |
| iC$_3$H$_7$Br | 2 | PDSA | decaline | 190 | 2 hrs | 38 | 12 | 88 |
| iC$_3$H$_7$OCOCl | 3 | PDDSA** | decaline | 190 | 2 hrs | 43 | 8 | 92 |
| iC$_3$H$_6$C$_6$H$_5$ | 4 | PDSA | decaline | 190 | 2 hrs | 34 | 11 | 89 |
| CH$_3$CH=CH$_2$ | 5 | Nafion-H | decaline | 190 | 2 hrs | 73 | 5 | 95 |
| iC$_3$H$_7$Cl | 6 | PDSA | decaline | 190 | 2 hrs | 54 | 2 | 98 |
| iC$_3$H$_6$C$_6$H$_5$ | 7 | PDSA | decaline | 190 | 4 hrs | 37 | 8 | 92 |
| pCH$_3$C$_6$H$_4$iC$_3$H$_7$ | 8 | PDSA | decaline | 190 | 4 hrs | 51 | 7 | 93 |
| iC$_3$H$_7$Cl | 11 | Nafion-H | gas phase | 220 | 10 sec | 34 | 7 | 93 |
| iC$_3$H$_7$Br | 12 | Nafion-H | gas phase | 220 | 10 sec | 30 | 8 | 92 |
| CH$_3$CH=CH$_2$ | 13 | Nafion-H | gas phase | 220 | 10 sec | 37 | 10 | 90 |
| iC$_3$H$_7$OH | 14 | Nafion-H | gas phase | 220 | 10 sec | 39 | 8 | 92 |
| pCH$_3$C$_6$H$_4$iC$_3$H$_7$ | 15 | Nafion-H | gas phase | 220 | 10 sec | 21 | 10 | 90 |

*PDSA = perfluorodecanesulfonic acid
**PDDSA = perfluorododecanesulfonic acid

I claim:

1. A process for the regionselective production of β-isopropylnaphthalene which comprises reacting naphthalene with a propylating agent over a superacidic solid or supported solid perfluorinated sulfonic acid catalyst.

2. A process according to claim 1, wherein the catalyst is a perfluorinated resinsulfonic acid.

3. A process according to claim 1, wherein the catalyst is a perfluorinated alkanesulfonic acid of C$_4$ to C$_{18}$ carbon atoms deposited on a suitable carrier.

4. A process to claim 1 in which the isopropylation is carried out in the liquid phase.

5. A process according to claim 1 in which the isopropylation is carried out in the as phase.

6. A process according to claim 1 in which isopropylation of naphthalene over aforementioned catalysts is effected via transalkylation with an isopropylated aromatic compound.

7. A process according to claim 1 in which the aromatic compound is isopropylbenzene, isopropyl toluenes, mixtures of diisopropyl or polyisopropylnaphthalenes.

8. A process for the conversion of mixtures of $\alpha$- and $\beta$-isopropylnaphthalene into essentially pure $\beta$-isopropylnaphthalene which comprises contacting the mixture with a superacidic solid or supported solid perfluorinated sulfonic acid catalyst.

* * * * *

UNITED STATES PATENT AND TRADEMARK OFFICE
CERTIFICATE OF CORRECTION

PATENT NO. : 4,288,646
DATED : September 8, 1981
INVENTOR(S) : George A. Olah

It is certified that error appears in the above—identified patent and that said Letters Patent is hereby corrected as shown below:

Column 5, line 65, reads "0.15 m./min.", should read
--0.15 ml/min.--

Column 6, line 55, reads "regionselective", should read
--regioselective--

Column 6, line 68, reads "as phase", should read
--gas phase--

Signed and Sealed this

Twenty-fourth Day of November 1981

[SEAL]

Attest:

GERALD J. MOSSINGHOFF

Attesting Officer   Commissioner of Patents and Trademarks